US010568583B2

(12) United States Patent
Brumfield et al.

(10) Patent No.: US 10,568,583 B2
(45) Date of Patent: Feb. 25, 2020

(54) METHODS AND SYSTEMS FOR PREDICTING HYPOVOLEMIC HYPOTENSIVE CONDITIONS RESULTING FROM BRADYCARDIA BEHAVIOR USING A PULSE VOLUME WAVEFORM

(71) Applicant: Intelomed, Inc., Wexford, PA (US)

(72) Inventors: Anne M. Brumfield, Cranberry Twp., PA (US); Jan K. Berkow, Allison Park, PA (US)

(73) Assignee: Intelomed, Inc., Cranberry Township, PA (US)

( * ) Notice: Subject to any disclaimer, the term of this patent is extended or adjusted under 35 U.S.C. 154(b) by 1105 days.

(21) Appl. No.: 14/302,411

(22) Filed: Jun. 11, 2014

(65) Prior Publication Data

US 2014/0364750 A1    Dec. 11, 2014

Related U.S. Application Data

(60) Provisional application No. 61/833,680, filed on Jun. 11, 2013.

(51) Int. Cl.
*A61B 5/02* (2006.01)
*A61B 5/00* (2006.01)
(Continued)

(52) U.S. Cl.
CPC ........ *A61B 5/7282* (2013.01); *A61B 5/02108* (2013.01); *A61B 5/02405* (2013.01);
(Continued)

(58) Field of Classification Search
CPC ..... A61B 5/7282; A61B 5/7221; A61B 5/725; A61B 5/4836; A61B 5/7214;
(Continued)

(56) References Cited

U.S. PATENT DOCUMENTS

| 4,450,527 A | 5/1984 | Sramek |
| 5,206,807 A | 4/1993 | Hatke et al. |

(Continued)

FOREIGN PATENT DOCUMENTS

| EP | 2392257 A2 | 12/2011 |
| EP | 1601287 B1 | 12/2012 |

(Continued)

OTHER PUBLICATIONS

European Patent Office, Supplementary EP Search Report issued in European Patent No. 14810662.8 dated Dec. 19, 2016, 8 pages.
(Continued)

*Primary Examiner* — Navin Natnithithadha
*Assistant Examiner* — Andrey Shostak
(74) *Attorney, Agent, or Firm* — Wood Herron & Evans LLP

(57) ABSTRACT

A method for identifying cardiac bradiacardia behavior may include acquiring pulse volume wave data from a sensor associated with a patient, and calculating metrics associated with peaks detected therein. The metrics may include changes in peak amplitudes of pulse volume peaks and in the times of occurrence of pulse volume peaks. Alternative metrics may include changes in frequency domain parameters derived from the time domain pulse volume wave data. Peak amplitude values may be compared to an amplitude baseline, and differences in successive peak occurrence times may be compared to a time baseline. Cardiac bradycardia behavior may be identified by a combination of a decrease in the pulse volume peak amplitude and an increase in successive peak occurrence times. A system to implement the method may include a computing device in data communication with a photo-plethysmograph. Alternative sensors may include a blood pressure cuff and an ECG device.

22 Claims, 6 Drawing Sheets

(51) Int. Cl.

| | |
|---|---|
| *A61B 5/021* | (2006.01) |
| *A61B 5/0464* | (2006.01) |
| *A61B 5/0245* | (2006.01) |
| *A61B 5/024* | (2006.01) |
| *G16H 50/30* | (2018.01) |
| *G16H 20/40* | (2018.01) |
| *A61B 5/0452* | (2006.01) |
| *A61B 5/0295* | (2006.01) |
| *A61B 5/0468* | (2006.01) |

(52) U.S. Cl.
CPC ...... *A61B 5/02416* (2013.01); *A61B 5/02455* (2013.01); *A61B 5/0464* (2013.01); *A61B 5/4836* (2013.01); *A61B 5/725* (2013.01); *A61B 5/7214* (2013.01); *A61B 5/7221* (2013.01); *A61B 5/7225* (2013.01); *A61B 5/7275* (2013.01); *G16H 20/40* (2018.01); *G16H 50/30* (2018.01); *A61B 5/0245* (2013.01); *A61B 5/0295* (2013.01); *A61B 5/0452* (2013.01); *A61B 5/0468* (2013.01); *A61B 5/7257* (2013.01)

(58) Field of Classification Search
CPC .............. A61B 5/7275; A61B 5/02416; A61B 5/02405; A61B 5/7225; A61B 5/0464; A61B 5/02455; A61B 5/02108; A61B 5/0245; A61B 5/0295; A61B 5/7257; A61B 5/0452; A61B 5/0468
See application file for complete search history.

(56) References Cited

U.S. PATENT DOCUMENTS

| | | | |
|---|---|---|---|
| 5,292,339 A | 3/1994 | Stephens et al. | |
| 5,370,122 A | 12/1994 | Kunig et al. | |
| 5,810,011 A | 9/1998 | Kunig | |
| 5,830,131 A | 11/1998 | Caro et al. | |
| 5,860,918 A | 1/1999 | Schradi et al. | |
| 5,865,756 A | 2/1999 | Peel, III | |
| 5,900,433 A | 5/1999 | Igo et al. | |
| 6,112,115 A | 8/2000 | Feldman et al. | |
| 6,126,595 A | 10/2000 | Amano et al. | |
| 6,217,522 B1 | 4/2001 | Shoshan | |
| 6,270,461 B1 | 8/2001 | Chio | |
| 6,287,608 B1 | 9/2001 | Levin et al. | |
| 6,315,735 B1 | 11/2001 | Joeken et al. | |
| 6,334,849 B1 | 1/2002 | Sunagawa | |
| 6,339,716 B1 | 1/2002 | Sawada et al. | |
| 6,371,922 B1 | 4/2002 | Baumann et al. | |
| 6,485,431 B1 | 11/2002 | Campbell | |
| 6,575,912 B1 | 6/2003 | Turcott | |
| 6,719,705 B2 | 4/2004 | Mills | |
| 6,776,764 B2 | 8/2004 | Pinsky | |
| 6,858,006 B2 | 2/2005 | MacCarter et al. | |
| 7,044,918 B2 | 5/2006 | Diab | |
| 7,285,090 B2 | 10/2007 | Stivoric et al. | |
| 7,324,848 B1 | 1/2008 | Turcott | |
| 7,328,053 B1 | 2/2008 | Diab et al. | |
| 7,330,750 B2 | 2/2008 | Erkkila et al. | |
| 7,678,057 B2 | 3/2010 | Berkow et al. | |
| 7,794,406 B2 | 9/2010 | Reisfeld et al. | |
| 8,423,108 B2 | 4/2013 | Berkow | |
| 2001/0049476 A1 | 12/2001 | Forstner | |
| 2002/0045806 A1 | 4/2002 | Baker et al. | |
| 2003/0167010 A1 | 9/2003 | Pinsky | |
| 2004/0039273 A1 | 2/2004 | Terry | |
| 2004/0249299 A1* | 12/2004 | Cobb .................. | A61B 5/0205 600/529 |
| 2005/0033129 A1 | 2/2005 | Edgar et al. | |
| 2005/0197675 A1 | 9/2005 | David et al. | |
| 2006/0167515 A1 | 7/2006 | Stickney et al. | |
| 2006/0293384 A1 | 12/2006 | Whewell | |
| 2007/0032732 A1 | 2/2007 | Shelley et al. | |
| 2007/0088222 A1 | 4/2007 | Berkow et al. | |
| 2007/0123787 A1 | 5/2007 | Kitajima et al. | |
| 2007/0255146 A1 | 11/2007 | Andrews et al. | |
| 2008/0167564 A1* | 7/2008 | Hete .................. | A61B 5/02405 600/508 |
| 2008/0228090 A1 | 9/2008 | Wariar et al. | |
| 2008/0255471 A1 | 10/2008 | Naghavi et al. | |
| 2008/0269625 A1 | 10/2008 | Halperin et al. | |
| 2009/0216141 A1* | 8/2009 | Fischell ............... | A61B 5/0031 600/509 |
| 2010/0081947 A1 | 4/2010 | Suzuki | |
| 2011/0245691 A1 | 10/2011 | Silber | |
| 2012/0029373 A1 | 2/2012 | Stadler et al. | |
| 2012/0029374 A1* | 2/2012 | Berkow ............. | A61B 5/02028 600/526 |
| 2012/0277608 A1 | 11/2012 | Schneider et al. | |
| 2012/0296219 A1* | 11/2012 | Chon .................. | A61B 5/02042 600/479 |
| 2013/0080489 A1 | 3/2013 | Ochs et al. | |
| 2013/0267858 A1 | 10/2013 | Berkow et al. | |
| 2014/0316278 A1* | 10/2014 | Addison ............ | A61B 5/02416 600/476 |
| 2016/0022204 A1* | 1/2016 | Mostov ................ | A61B 5/0002 600/301 |

FOREIGN PATENT DOCUMENTS

| | | |
|---|---|---|
| EP | 2540222 A2 | 1/2013 |
| WO | 03/077854 A2 | 9/2003 |
| WO | 04/084720 A2 | 10/2004 |
| WO | 2005/107584 A1 | 11/2005 |
| WO | 2014/143962 A2 | 9/2014 |

OTHER PUBLICATIONS

Cruz et al., Algorithm Fusion for the Early Detection of Apnea-Bradycardia in Preterm Infants, Computers in Cardiology, (Sep. 17, 2006), 473-476 <http://ieeexplore.ieee.org/xpl/login.jsp?arnumber=4511891>.
Feiseel et al., Respiratory Variation of Plethysmography Signal with a Pulse Oximeter: New Predictive Parameters of Fluid Responsiveness?, Proceedings of the American Thoracic Society, (Apr. 2006), 3:A295.
Kim et al., Can Cardiac Contractility be Estimated by an Inspiratory Hold Manueuver?, Proceedings of the American Thoracic Society, (Apr. 2006), 3:A296.
Kim et al., Determinates of Arterial Pulse Pressure and Stroke Volume Variation during Positive-Pressure Ventilation, Proceedings of the American Thoracic Society, (Apr. 2006), 3:A297.
Lamia et al., Brachial Pulse Pressure is Related to Total Arterial Compliance and Stroke Volume in ICU Patients: An Arterial Tonometric Study, Proceedings of the American Thoracic Society, (Apr. 2006), 3:A296.
Monnet et al., Measuring Aortic Diameter is Essential for Assessing Fluid Challenge by Esphageal Doppler, Proceedings of the American Thoracic Society, (Apr. 2006), 3:A296.
Pravisani et al., Short Term Prediction of Severe Bradycardia in Premature Newborns, Computers in Cardiology, (Sep. 21, 2003), 725-728.
Portet et al., Evaluation of On-Line Bradycardia Boundary Detectors from Neonatal Clinical Data, Conf IEEE Engl Med Biol Soc., (Aug. 22, 2007), 3288-3291.
Ridel et al., Prediction of Fluid Responsiveness in Spontaneously Breathing Patients: Response to Passive Leg Raising Measured by Pulse Contour Cardiac Output, Proceedings of the American Thoracic Society, (Apr. 2006), 3:A295.
Zamanian et al., Assessment of Cardiac Function and Ventilatory Efficiency by Noninvasive CO2 Monitoring during Reduction of Ventilatory Support in Patients with CHF, Proceedings of the American Thoracic Society, (Apr. 2006), 3:A296.
International Search Report for PCT/US2014/040890 dated Nov. 4, 2014.
International Search Report for PCT/US2014/042012 dated Nov. 10, 2014.

(56) References Cited

OTHER PUBLICATIONS

International Search Report for PCT/US2014/050771 dated Dec. 1, 2014.

* cited by examiner

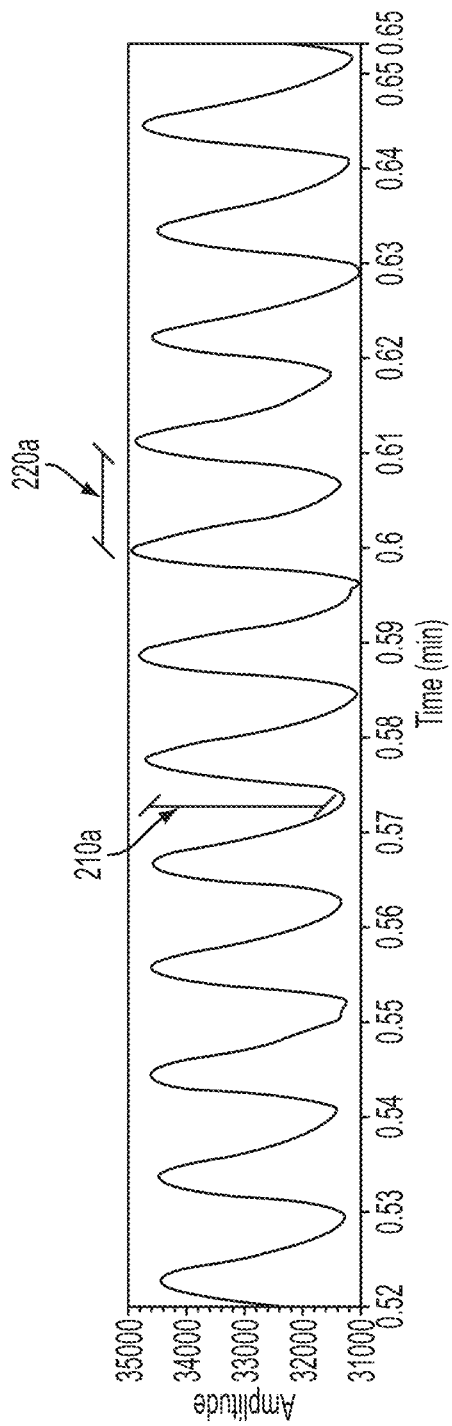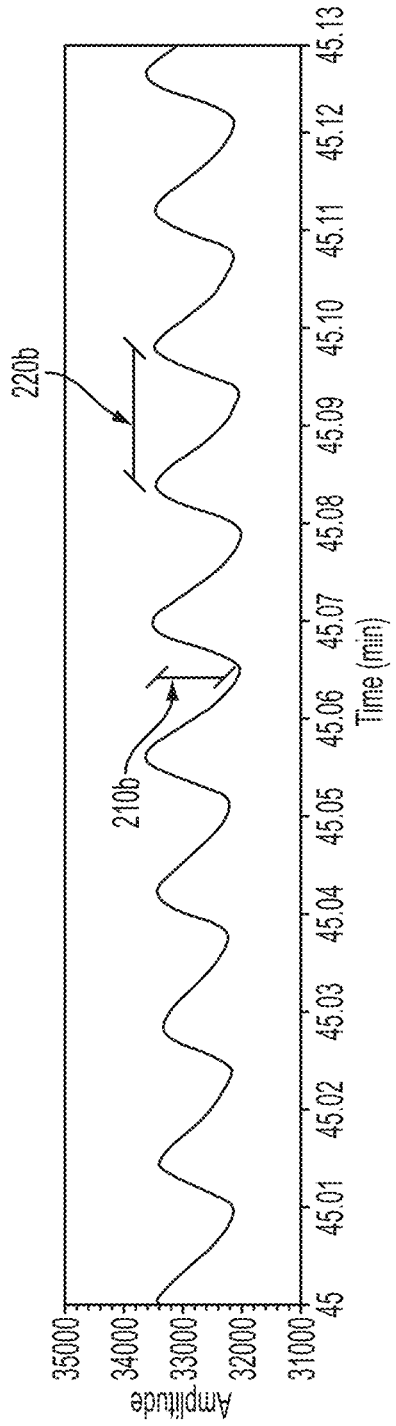
FIG. 2A
FIG. 2B

METHODS AND SYSTEMS FOR PREDICTING HYPOVOLEMIC HYPOTENSIVE CONDITIONS RESULTING FROM BRADYCARDIA BEHAVIOR USING A PULSE VOLUME WAVEFORM

CLAIM OF PRIORITY

This application claims priority to and benefit of U.S. Provisional Application Ser. No. 61/833,680 filed Jun. 11, 2013 entitled "Detection and Quantification of Bradycardia Behavior Using a Pulse Volume Waveform," the disclosure of which is incorporated herein by reference in its entirety.

BACKGROUND

Cardiac electrophysiology refers to the orchestration of electrical pulses that cause the myocardium to contract in a coordinated manner to efficiently pump blood into the arterial tree. Suboptimal physiological alterations that effect the cardiac myocyte milieu can compromise the myocyte function and adversely affect the electrical conduction tissue. As a result, the electrical pulse sequences of the heart may be altered leading to abnormal cardiac sinus rhythms that can cause dysynchronous or suboptimal myocardial contractile behaviors.

Contractile abnormalities, as observed in electrocardiography (ECG) traces, can be characterized as irregular heartbeats or arrhythmias that may manifest as tachycardia, bradycardia, palpitations, or fibrillation. Practitioners having domain expertise in electrocardiology may be able to differentiate abnormal ECG patterns from normal ECG patterns. Practitioners may also be adept at recognizing specific types of arrhythmias via PQRST ECG tracing patterns or behaviors. These ECG patterns provide information regarding the nature or cause of the arrhythmia thereby enabling more effective cardiac health treatment management. For example, arrhythmias can be used to identify numerous forms of physiological dysfunction that include thyroid dysfunction, anemia, myocardial ischemic conditions, and multiple electrical pathways that result in poor cardiac function. In these examples, the recognition of an arrhythmia serves as part of a patient assessment to either diagnose a pathology, thereby enabling its treatment, or to predict onset of a pathology, thereby enabling overall patient management.

Alternatively, cardiac arrhythmias can result from myocardial ischemic conditions and result in decreased cardiac output. Decreased cardiac output may contribute to a hemodynamically unstable physiological state and predispose a patient to life threatening conditions. As such, a second purpose of arrhythmia detection may be to serve as part of a real-time hemodynamic monitoring tool. Integral to facilitating this clinical utility is the ability to characterize the dysrhythmia behavior in terms of the severity of its adverse effect on cardiovascular hemodynamics. Use of physiological feedback of dysfunctional cardiac behavior in concert with other hemodynamic parameters can provide valuable information to characterize the overall physiologic behavior or state of a patient. Measures related to severity of cardiac related hemodynamic instability measures can provide valuable real-time feedback as a part of a hemodynamic monitor to manage patient stability and/or determine appropriate intervention for this purpose.

Cardiac dysrhythmia may also manifest as bradycardia that can result from a hypovolemic state of the patient. The pathogenesis of a hypovolemic response may initially begin with a rapid parasympathetic response to activate the cardiac compensatory mechanism to defend the arterial system against fluid translocation as a basis to preserve pressure and flow. The rapid parasympathetic response may continue until longer term baroreceptor instigated neural activation occurs and more sustained cardiac and vasomotor compensatory mechanisms are engaged. In some instances, a paradoxical bradycardic response can occur reflective of a sympathetic inhibition (also referred to as a Bezold-Jarische reflex) and vasodilation, which exacerbates the hypotensive response. Such vasodilation can occur in response to various forms of shock. In addition, the vasodilation may occur in end-stage renal disease patients undergoing fluid removal during hemodialysis treatments during which a bradycardia-like response can be observed accompanying an induced hypotensive acute condition.

The pulse waveform obtained from a pulse oximeter, also referred to as a photoplethysmograph, is a mature technology that can be used as a standalone monitor or readily integrated as part of a hemodynamic monitoring system. The photoplethysmograph is not capable of capturing electrophysiological signals. However, measures derived from the pulse waveform can be used to assess changes in tissue perfusion and autonomic nervous system stress patterns based upon temporal alterations of the pulse waveform features. The degree of specific waveform feature abnormality and the frequency of incidence of such anomalous waveform features can be used to recognize patient specific levels of decreasing compensation. Decreased hydrodynamic compensation may be indicative of the severity of the adverse hemodynamic impact resulting from cardiac dysfunction. The resultant clinical utility may be to provide either a standalone hemodynamic monitoring device or a component of a hemodynamic monitoring device that enables real-time feedback as a hemodynamic instability monitor based upon detecting threshold limits in pre-identified photoplethysmograph pulse waveform features.

SUMMARY

In an embodiment, a method for predicting a hypovolemic hypotensive condition resulting from cardiac bradycardia behavior may include, receiving, by a computing device, a biological signal emulating an arterial pulse wave from a sensor in data communication with a human body, determining, by the computing device, a plurality of pulse rate metrics from the biological signal, determining, by the computing device, a plurality of pulse strength metrics from the biological signal, determining, by the computing device, a plurality of pulse rate differences, wherein each pulse rate difference is determined from a first pulse rate metric and a pulse rate baseline, determining, by the computing device, a plurality of pulse strength differences, wherein each pulse strength difference is determined from a first pulse strength metric and a pulse strength baseline, and predicting, by the computing device, a hypovolemic hypotensive condition resulting from cardiac bradycardia behavior in the human body in response to at least one anomalous pulse rate difference and at least one anomalous pulse strength difference.

In an embodiment, a system for predicting a hypovolemic hypotensive condition resulting from cardiac bradycardia behavior may include at least one sensor in data communication with a human body, the at least one sensor configured to receive a biological signal emulating an arterial pulse wave from the human body, a computing device in operable communication with the at least one sensor, a non-transitory, computer-readable storage medium in operable communication with the computing device, an input device in operable communication with the computing device, and an output device in operable communication with the computing device. Further, the computer-readable storage medium of the computing device may contain one or more programming instructions that, when executed, cause the computing device to receive a biological signal emulating an arterial pulse wave from the sensor, determine a plurality of pulse rate metrics from the biological signal, determine a plurality of pulse strength metrics from the biological signal, determine a plurality of pulse rate differences, wherein each pulse rate difference is determined from a first pulse rate metric and a pulse rate baseline, determine a plurality of pulse strength differences, wherein each pulse strength difference is determined from a first pulse strength metric and a pulse strength baseline, and predict a hypovolemic hypotensive condition resulting from cardiac bradycardia behavior in the human body in response to at least one anomalous pulse rate difference and at least one anomalous pulse strength difference.

BRIEF DESCRIPTION OF THE DRAWINGS

FIG. 2A depicts a normal human pulse volume waveform in accordance with some embodiments.

FIG. 2B depicts a human pulse volume waveform showing bradycardia in accordance with some embodiments.

DETAILED DESCRIPTION

Figure 1A:
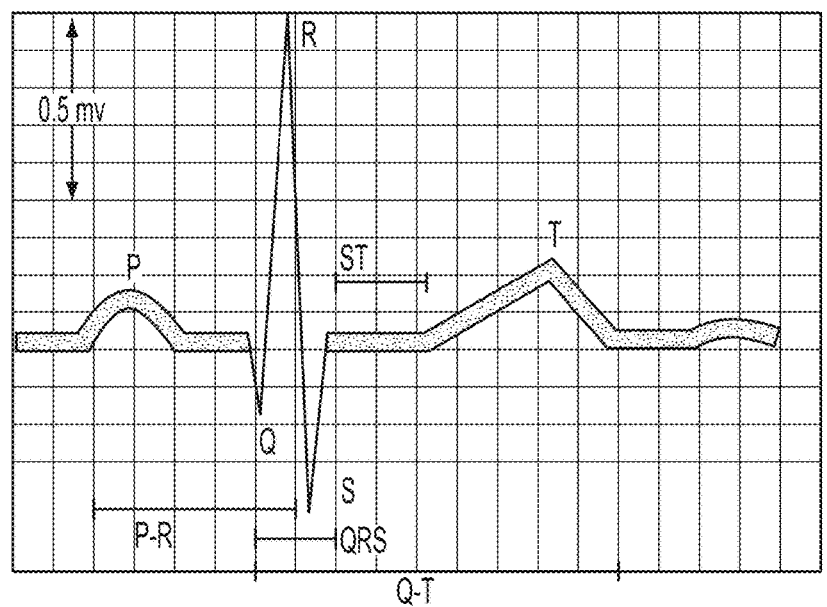
FIG. 1A depicts a normal human ECG tracing in accordance with some embodiments.

As disclosed above, hypovolemia may be one of the frequent causes of arrhythmias. In some instances, hypovolemic shock may be induced during hemodialysis. Although tachycardia may frequently be present during hemodialysis, bradycardia may also be manifested due to volemic loss. While an ECG trace may be used by a health care provider to monitor and diagnose the specific electro-cardio-behavior responsible for specific arrhithimias, such a device may not provide information regarding anomalies in the hemodynamics of patient blood-flow.

A pulse oximeter is a sensor capable of detecting the pulsatile flow of blood through the vasculature and producing a pulse waveform that can emulate an arterial pulse wave from a patient. Such a sensor can be used as a standalone monitoring device or may be readily integrated in a hemodynamic monitoring system. One non-limiting example of a pulse oximeter may include a photoplethysmograph. The pulse oximeter may not be capable of capturing cardiac electrophysiology signals. However, cardiac dysrhythmia, such as bradycardia, may be deduced from alterations in normal pulse waveform patterns due to the effects of cardiac dysrhythmia on blood flow. The severity of the impact of such cardiac dysrhythmia on patient hemodynamic functions may be characterized by anomalous features in the pulse waveform patterns. In some non-limiting examples, the impact of cardiac dysrhythmia on hemodynamic functions may be characterized by specific anomalous pulse waveform features and the frequency of their occurrence. Methods of analyzing pulse volume waveform features derived from pulse oximeters (or similar devices) may be used by a health care provider to monitor hemodynamic instability in a patient, such as during a therapeutic procedure. Such methods may be embodied either in a standalone device or as a non-limiting component of a hemodynamic monitoring system.

An ECG or other heart rate monitoring source alone or in concert with a blood pressure measurement device, including one or more hemodynamic measurement devices, has been used to detect bradycardic behavior. Presently, techniques have been developed solely to recognizes bradycardia behavior, for example when the heart rate has dropped below 50 bpm (beats per minute) as may occur during a sinus bradycardia condition. The methods and systems disclosed herein, however, may be useful in recognizing pre-symptomatic conditions that, if left unchecked, may dispose a patient to bradycardic behavior and the hemodynamic impacts thereof.

Thus, disclosed herein are embodiments of a real-time method to detect and quantify cardiac bradycardia by applying an algorithm-based "toolkit" to a pulse waveform captured from a photoplethysmograph (PPG) or other source producing signals related to a pulse volume waveform, such as an ECG or blood pressure cuff. The toolkit may include functions to assess changes in one or more features of a patient's pulse volume waveform morphology to identify bradycardia patterns typically recognized using an ECG trace. Non-limiting examples of pulse waveform features may include a pulse amplitude and an inter-pulse occurrence time.

In some embodiments, such features may be compared to one or more pulse waveform features maintained in one or more feature databases or feature libraries. Such feature databases or libraries may be stored in a device used to monitor the hemodynamic status of one or more patients. Alternatively, such feature databases or libraries may be stored in devices accessible to the device used to monitor the hemodynamic status of one or more patients. Such storage devices may include removable storage media, such as a disk or a thumb drive, or a server remote from the monitoring device. A remote server may be in data communication with the monitoring device over the internet, an intranet, a local personal network, or over wireless connection such as a telephonic connection or an RF connection. In one non-limiting example, a feature database may be derived from data obtained from a population of patients demonstrating such features. In another non-limiting example, a feature database may be derived from one or more animal models. In yet another non-limiting example, a feature database may be derived from data obtained from the same patient being monitored. In still another non-limiting example, a feature database may be derived from one or more mathematical models.

FIG. 1A depicts a typical normal human ECG trace, illustrating features often used by health care providers to assess the nature of cardiac contractility. The ECG trace is frequently described in terms of the PQRST features, as indicated in FIG. 1A. The P feature generally corresponds to the depolarization of the atria of the heart, and is typically initiated at the sinoatrial node. The QRS complex typically corresponds to ventricular depolarization and typically is initiated at the atrioventricular node. The P-R time interval generally represents an electrical conduction time lag between the onset of atrial contraction and the onset of ventricular contraction. The Q-R time interval generally is the total time required for complete ventricular electrical depolarization and hence ventricular contraction. The T feature corresponds to the repolarization of the ventricular tissue, and the S-T interval is a lag time between ventricular depolarization and the onset of ventricular re-polarization. Other features may be found in an abnormal ECG depending on the pathology. Not shown in FIG. 1A is an R-R interval that generally corresponds to the time between successive ventricular contractions. For a normally functioning heart, the R-R interval is associated with the heart rate.

Figure 1B:
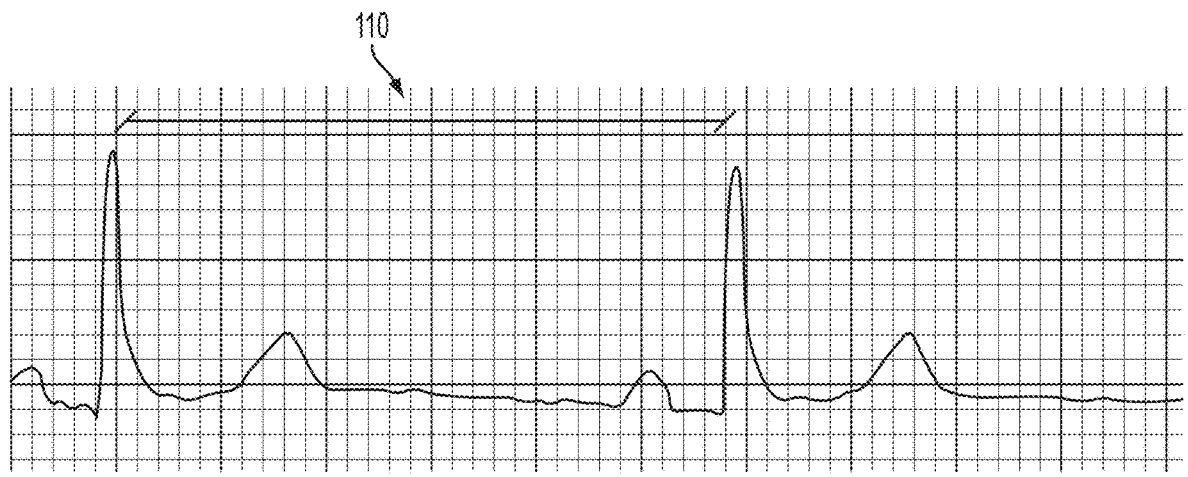
FIG. 1B depicts a human ECG tracing illustrating bradycardia in accordance with some embodiments.

FIG. 1B illustrates an ECG trace characteristic of bradycardia. In FIG. 1B, two PQRST features may be observed. Although the PQRST features in FIG. 1B appear superficially the same as depicted in FIG. 1A, the R-R interval 110 appears significantly longer than may be found in normative heart rhythms. Typically, the resting heart rate is about 50 bpm (beats per minute) to about 60 bpm, providing an R-R interval of about 1000 msec to about 1200 msec. It may be understood that athletically trained individuals may display unusually long R-R intervals, such as about 2200 msec. Clinically, however, a waking heart beat below 40 bpm (R-R interval of about 1500 msec) is frequently considered pathological.

FIGS. 2A and 2B illustrate human pulse volume waveforms (for example, from a plethysmograph) of normative heart rates and bradycardic heart rates, respectively. The pulse volume waveform in FIG. 2A illustrates normal pulse volume waveforms that may be characterized by a series of pulse volume peak amplitudes 210a and a difference in the occurrence time between success peaks 220a. It may be understood that a difference in the occurrence time between success peaks 220a is related to the R-R interval directly observable in an ECG trace. The structure of the pulse volume waveforms that may be present during a bradycardic event is depicted in FIG. 2B. The bradycardic pulse volume waveforms may also be characterized by pulse volume peak amplitudes 210b and differences in the occurrence time between successive peaks 220b. It may be observed that the amplitudes of the bradycardic wave forms 220b appear significantly smaller than the amplitudes of the normal waveforms 220a. Additionally, the normative difference in the occurrence time between successive peaks 220a (a measure of the normative R-R interval) appears less than the bardycardial difference in the occurrence time between successive peaks 220b (a measure of the bradycardic R-R interval).

The methods disclosed herein may incorporate data derived from time domain data or frequency domain data obtained from the biological signal. Time domain data may include data from the biological signal that may be characterized by an amplitude measure of the signal that may change over time. Frequency domain data may include data derived from a frequency analysis of the biological signal limited to within one or more time windows. In various embodiments, a Fast-Fourier Transform (FFT) algorithm may be applied to the biological signal in one or more time windows, thereby producing one or more power spectra. Each power spectrum may be characterized by one or more frequency bands, each band having a frequency band power. The one or more frequency bands within a power spectrum may be further filtered using one or more filtering or smoothing techniques as known in the art. Such smoothing filters may include, without limitation, a Butterworth filter, a Chebyshev filter, a Bessel filter, an elliptical filter, a custom low pass filter, and techniques using moving averages. In alternative embodiments, a wavelet transformation may be used for such a frequency domain determination. One skilled in the art of signal processing would recognize that such a frequency analysis may further include pre-processing the biological signal data within the one or more time windows to reduce effects of finite window aliasing on the biological signal.

Figure 3A:
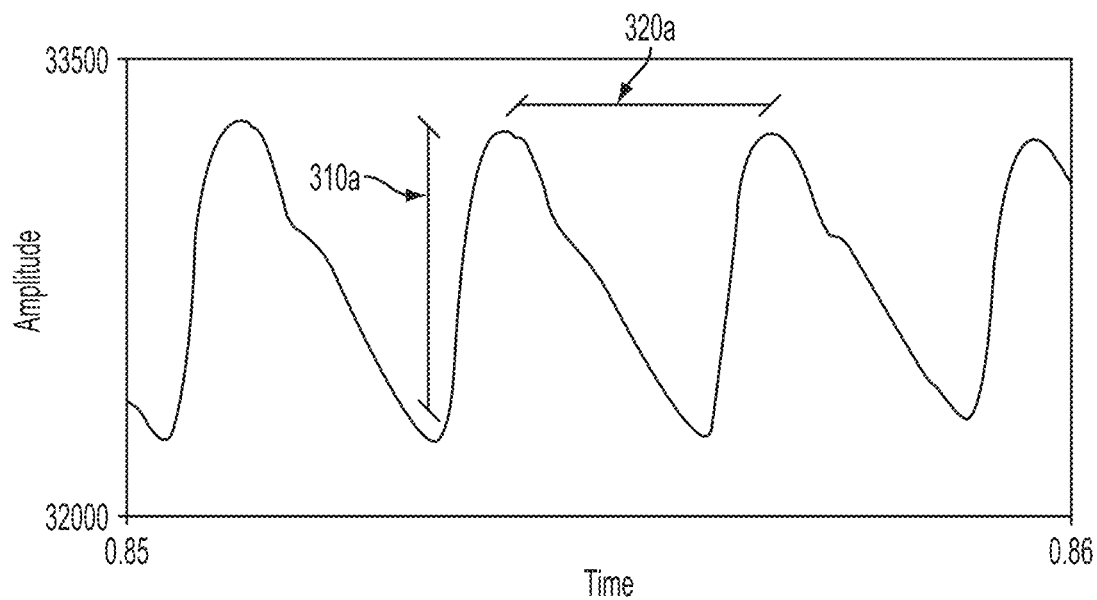
FIGS. 3A and 3B depict a human pulse volume waveform in the time domain and its respective spectral analysis in the frequency domain in accordance with some embodiments.
Figure 3B:
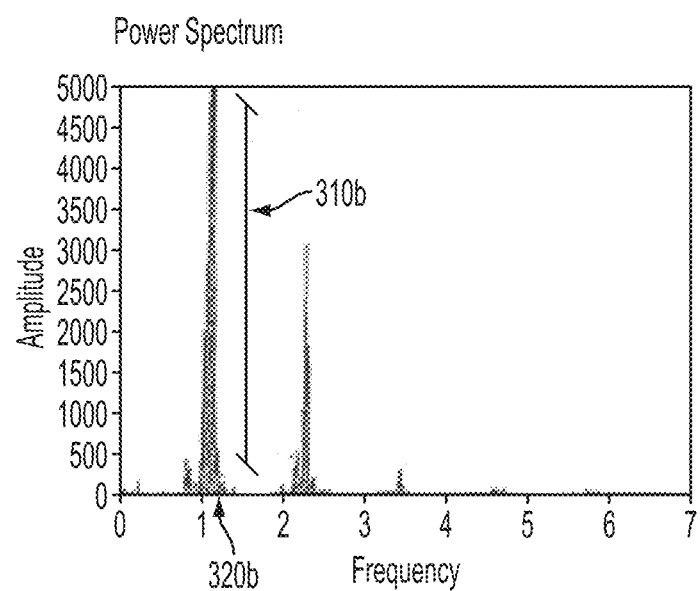

FIGS. 3A and 3B depict a trace of pulse volume waveforms and a power spectrum analysis of the same waveforms, respectively. The pulse volume waveforms in FIG. 3A may be characterized by peak amplitudes 310a and differences in occurrence times 320a between successive waveform peaks (corresponding to an ECG R-R interval). It may be understood that the pulse volume waveforms in FIG. 3A correspond to data received in the time domain from a pulse volume sensor such as a photoplethysmograph.

The power spectrum analysis graph in FIG. 3B may be characterized by a series of peaks occurring at specific frequencies such as a primary frequency corresponding to a heart rate 320b. Each frequency peak may further be characterized by its peak power 310b. It may be understood that the power spectrum graph in FIG. 3B presents equivalent data in the frequency domain to the time domain data in FIG. 3A.

In some embodiments, a pulse rate metric may be calculated from a plurality of time difference values 320a in the time domain. Alternatively, the pulse rate metric may be calculated from a primary power spectrum frequency 320b in the frequency domain. Similarly, a pulse strength metric may be calculated from a plurality of pulse volume waveform peak amplitudes 310a in the time domain or from the peak power 310b at the primary power spectrum frequency 320b in the frequency domain. It may be appreciated that the choice of time domain or frequency domain calculations may be dependent on the quality of data from the pulse volume sensor, the speed at which the calculations may be made, or other factors. It may also be recognized that more complex methods may use both time domain and equivalent frequency domain data together for improved system performance.

Figure 4:
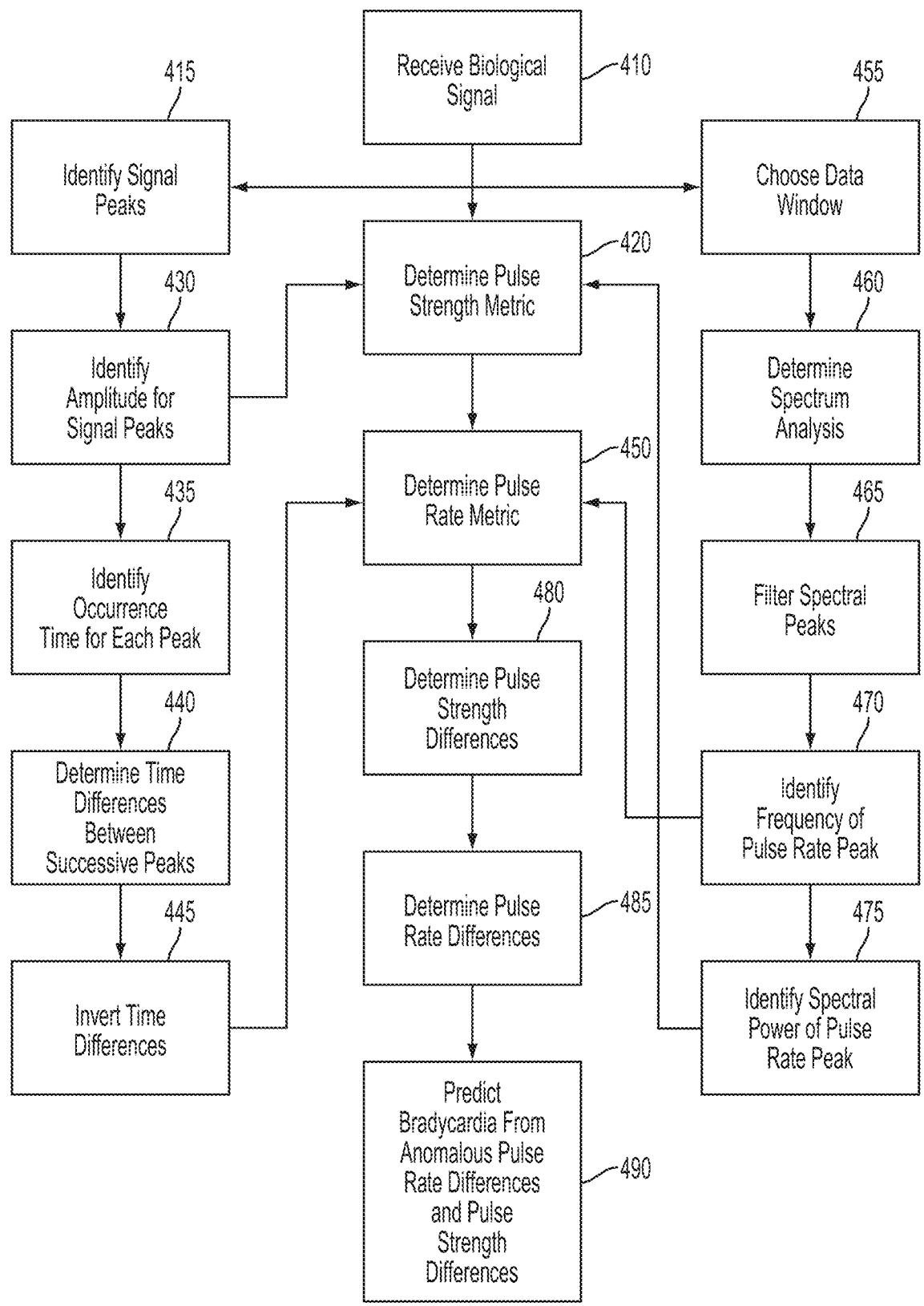
FIG. 4 is a flow chart for a method of predicting a hypovolemic hypotensive condition resulting from cardiac bradycardia behavior in accordance with some embodiments.

FIG. 4 constitutes a flow chart of a method for predicting a hypovolemic hypotensive condition resulting from cardiac bradycardia behavior from a plurality of pulse volume waveforms.

A biological signal, emulating a plurality of arterial pulse volume waveforms, may be received 410 by a computing device from a sensor associated with a human body such as from a patient undergoing a therapeutic procedure. Non-limiting embodiments of such a sensor may include one or more of a plethysmograph, a photoplethysmograph, a transmittance photo-optic sensor, a reflective photo-optic sensor, a pressure transducer, a tonometry device, a strain gauge, an ultrasound device, an electrical impedance measurement device, a radar device, a sphygmomanometer, and an ECG device. Such sensors may be in physical contact with the patient's skin surface, within the patient, or may be placed at some distance from the patient.

The biological signal received 410 by the computing device may be processed by the computing device according to any method known in the arts of electronic signal acquisition. Post-acquisition conditioning of the acquired biological signal may include any of a variety of methods implemented in circuitry, firmware, software, or any combination thereof to improve signal quality and sensitivity. In various non-limiting embodiments, such conditioning may include one or more of noise filtering, signal amplification, and signal conversion from an analog to a digital format.

The biological signal, either in a raw form (without post-acquisition conditioning) or in a conditioned form may be used by the computing device to determine a plurality of pulse strength metrics 420 as well as a plurality of pulse rate metrics 450. The computing device may determine a plurality of pulse strength differences 480, wherein each pulse strength difference is determined from a first pulse strength metric and a pulse strength baseline. The computing device may further determine a plurality of pulse rate differences 485, wherein each pulse rate difference is determined from a first pulse rate metric and a pulse rate baseline.

In some non-limiting embodiments, the pulse strength baseline may be a value chosen by a computing device operator or a health care provider. In alternative non-limiting embodiments, the pulse strength baseline may be determined by the computing device. The pulse strength baseline may be determined in the time domain or in the frequency domain.

In the time domain, a non-limiting example of determining the pulse strength baseline may include identifying a plurality of signal peaks occurring within a data window within the biological signal received from the patient, identifying an amplitude for each of the plurality of signal peaks, and determining a pulse strength baseline from the plurality of signal peaks. In one non-limiting example, the pulse strength baseline may be determine from an average peak amplitude of the plurality of signal peaks. In another non-limiting example, the pulse strength baseline may be determine from a maximum peak amplitude of the plurality of signal peaks. In yet another non-limiting example, the pulse strength baseline may be determined from a plurality of biological signals, wherein each biological signal may be obtained from one of a plurality of patients or normal humans. Thus, average or maximal peak amplitude values over a number of humans may be used to obtain the pulse strength baseline. In one non-limiting example, the windowed biological signal may be chosen during a period of normative (non-pathological) cardiac activity of the patient.

The data window for acquiring the biological signal used to determine one or more baselines may be characterized by one or more of a start time, a stop time, and a window duration. In some non-limiting examples, the data window may have a window duration of about 1 minute to about 24 hours. Non-limiting examples of such time window durations may include time durations of about 1 minute, about 2 minutes, about 5 minutes, about 10 minutes, about 20 minutes, about 30 minutes, about 1 hour, about 2 hours, about 5 hours, about 10 hours, about 20 hours, about 24 hours, and ranges between any two of these values including endpoints. Values characterizing the data window may include static values accessible by the computing device, one or more values supplied by a computing device user or health care provider, or a combination thereof. In some non-limiting examples, the data window may be chosen to include at least one respiratory period, in which the respiratory period may be calculated as an average respiratory period of the patient or an average respiratory period of a plurality of patients.

In the frequency domain, a non-limiting example of determining the pulse strength baseline may include determining a spectrum analysis of a portion of the biological signal within a data window that includes a period of a normative cardiac rhythm of the human body, filtering one or more spectral peaks from the spectrum analysis, identifying a spectral peak having a central frequency of about a pulse rate of the human body from the spectrum analysis, and determining the pulse strength baseline from a spectral power of the spectral peak. In an alternative example, the pulse strength baseline may be determined from a plurality of spectrum analyses, each spectral analysis corresponding to a portion of the biological signal within each of a plurality of data windows, wherein each of the plurality of data windows includes a period of a normative cardiac rhythm of the human body, filtering one or more of a plurality of spectral peaks, each of the plurality of spectral peaks being obtained from one of the plurality of spectrum analyses, identifying a plurality of spectral peaks, each spectral peak having a central frequency of about a pulse rate of the human body from one of the plurality of spectrum analyses, and determining the pulse strength baseline from an average of a plurality of spectral powers, each spectral power being determined from one of the plurality of spectral peaks. Alternatively, spectrum analyses may be performed on a portion of biological signals obtained from a plurality of patients, and the pulse strength baseline may be determines from an average spectral power of the plurality of spectral powers corresponding to the pulse rates of each of the patients.

It may be understood that the window used to acquire the biological signal or signals for a spectrum analysis may have the same characteristics disclosed above for a data window used with respect to the time domain determination of the pulse strength baseline.

In some non-limiting embodiments, the pulse rate baseline may be a value chosen by a computing device operator or a health care provider. In alternative non-limiting embodiments, the pulse rate baseline may be determined by the computing device. The pulse rate baseline may also be determined in the time domain or in the frequency domain.

In the time domain, a non-limiting example of determining the pulse rate baseline may include identifying a plurality of signal peaks within a data window of the biological signal, wherein the data window includes a period of a normative cardiac rhythm, identifying a time occurrence for each of the plurality of signal peaks, determining a plurality of time differences, wherein each time difference is determined from a first time occurrence of the first peak and a second time occurrence of a second peak, determining an average time difference from the plurality of time differences, and determining an inverse (or mathematical reciprocal) of the average time difference. Thus, the method may include determining a plurality of peak-to-peak time differences (equivalent to a plurality of R-R intervals of an ECG), calculating an average peak-to-peak time difference, and inverting the average time difference to produce an average rate.

In an alternative time domain method, a method of determining a pulse rate baseline may include determining a plurality of peak-to-peak time differences (equivalent to a plurality of R-R intervals of an ECG), determining an inverse of each of the time differences to form a plurality of rates, and calculating an average of the rates.

In yet another alternative time domain method, the pulse rate baseline may include identifying a plurality of signal peaks within a data window of the biological signal, wherein the data window includes a period of a normative cardiac rhythm of the human body, identifying a time occurrence for each of the plurality of signal peaks, determining plurality of time differences, wherein each time difference is determined from a first time occurrence of the first peak and a second time occurrence of a second peak, identifying a maximum time difference of the plurality of time differences and determining an inverse of the maximum time difference.

In still another non-limiting embodiment, determining the pulse rate baseline may include determining an average pulse rate baseline from a plurality of biological signals, wherein each of the plurality of biological signals is obtained from one of a plurality of human bodies, thereby creating a baseline across a number of patients. In still another non-limiting embodiment, determining the pulse rate baseline may include determining an average of a normative pulse rate obtained from the human body using non-volumetric data, such as from an ECG device. In still another non-limiting embodiment, determining the pulse rate baseline comprises determining an average of a plurality of normative pulse rates, wherein each of the plurality of normative pulse rates is obtained from one of a plurality of human bodies.

In the frequency domain, a non-limiting example of determining the pulse rate baseline may include determining a spectrum analysis of a portion of the biological signal within a data window that includes a period of a normative cardiac rhythm of the human body, filtering one or more spectral peaks from the spectrum analysis, and identifying a spectral peak having a central frequency of about a pulse rate of the human body from the spectrum analysis. In an alternative example, the pulse rate baseline may be determined from a plurality of spectrum analyses, each spectral analysis corresponding to a portion of the biological signal within each of a plurality of data windows, wherein each of the plurality of data windows includes a period of a normative cardiac rhythm of the human body, filtering one or more of a plurality of spectral peaks, each of the plurality of spectral peaks being obtained from one of the plurality of spectrum analyses, identifying a plurality of spectral peaks, each spectral peak having a central frequency of about a pulse rate of the human body from one of the plurality of spectrum analyses, and determining the pulse rate baseline from an average of a plurality of central peak frequencies. Alternatively, spectrum analyses may be performed on a portion of biological signals obtained from a plurality of patients, and the pulse rate baseline may be determines from an average peak frequency corresponding to the pulse rates of each of the patients.

It may be understood that the window used to acquire the biological signal or signals for a time domain or frequency domain determination of the pulse rate baseline may have the same characteristics disclosed above for a data window used with respect to the time domain determination of the pulse strength baseline.

Values for the pulse rate baseline and pulse strength baseline may be determined from average values of their respective metrics over one or more data windows. In some non-limiting examples, a variance measurement may be determined for an average pulse rate baseline value and a variance measurement may also be determined for an average pulse strength baseline value. In some non-limiting examples, a pulse rate baseline value derived from an average pulse rate value may be rejected if the equivalent variance is greater than an acceptance criterion. Similarly, in some non-limiting examples, a pulse strength baseline value derived from an average pulse strength value may be rejected if the equivalent variance is greater than an acceptance criterion. Under such rejection conditions, new data windows may be chosen for determining average values for one or more of the pulse rate baseline and pulse strength baseline.

Based on the pulse strength differences and the pulse rate difference, the computing device may predict 490 a hypovolemic hypotensive condition resulting from cardiac bradycardia behavior in the human body based on at least one anomalous value of the pulse rate difference and at least one anomalous value of the pulse strength difference. In one non-limiting example, an anomalous value of a pulse rate difference may be a value of a pulse rate difference greater than a pulse rate threshold value. In another non-limiting example, an anomalous value of a pulse strength difference may be a value of a pulse strength difference greater than a pulse strength threshold value.

In some non-limiting embodiments, one or more of the pulse strength threshold value and the pulse rate threshold value may be chosen by a computing device operator or a health care provider. In alternative non-limiting embodiments, such threshold values may be determined by the computing device.

In some non-limiting examples, the pulse rate threshold may be determined by subtracting a pulse rate factor times the pulse rate baseline from the pulse rate baseline. In some non-limiting examples, the pulse rate factor may have a value greater than zero and less than or equal to 1. Examples of such pulse rate factors may include 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, and ranges between any two of these values including endpoints. In some non-limiting examples, the pulse rate factor may have a value of about 0.15. In some non-limiting embodiments, the pulse rate factor may be stored in a library of pulse rate baseline factors. Such a library of pulse rate baseline factors may be stored in one or more memory devices in data communication with the computing device.

In some non-limiting examples, the pulse strength threshold may be determined by subtracting a pulse strength factor times the pulse strength baseline from the pulse strength baseline. In some non-limiting examples, the pulse strength factor may have a value greater than zero and less than or equal to 1. Examples of such pulse strength factors may include 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, and ranges between any two of these values including endpoints. In some non-limiting examples, the pulse strength factor may have a value of about 0.15. In some non-limiting embodiments, the pulse strength factor may be stored in a library of pulse strength baseline factors. Such a library of pulse strength baseline factors may be stored in one or more memory devices in data communication with the computing device.

Returning to FIG. 4, the computing device may determine 420 a pulse strength metric and determine 450 a pulse rate metric.

As disclosed herein, a pulse strength metric may be determined 420 from time domain data or frequency domain data. In some non-limiting examples, a time domain pulse strength metric may be determined by identifying 415, by the computing device, a plurality of signal peaks within the biological signal; and identifying 430, by the computing device, an amplitude for each of the plurality of signal peaks. In some embodiments, the computing device may identify 415 a plurality of signal peaks by determining a maximum amplitude within a time window that moves along the received 410 biological signal. In another embodiment, the computing device may identify 415 a plurality of signal peaks by fitting a portion of the biological signal within a window to a peak function, such as a parabola. In another embodiment, the computing device may identify 415 a plurality of signal peaks by calculating a time derivative of a portion of the biological signal within a window and determine the position of zero-crossing points.

In some embodiments the computing device may identify 430 an amplitude for each of the plurality of signal peaks by identifying the maximum amplitude of the peak. In another embodiment, computing device may identify 430 an amplitude for each of the plurality of signal peaks by smoothing the data around the peak using a smoothing filter and identifying the maximum amplitude of the smoothed peak. In some non-limiting examples, the computing device may identify 430 an amplitude for each of the plurality of signal peaks by calculating an average amplitude of a plurality of amplitudes around each of the signal peaks.

In one example, the computing device may calculate an average amplitude of a plurality of amplitudes around each of the signal peaks within a data window. In one non-limiting example, the data window may comprise a time duration equal to at least one respiratory cycle of a patient being monitored. In one non-limiting example, the data window may have a duration of about 5 seconds to about 30 seconds. Non-limiting examples of such a window durations may include about 5 seconds, about 10 seconds, about 15 seconds, about 20 seconds, about 25 seconds, about 30 seconds, and ranges between any two of these values including endpoints. In one non-limiting example, the data window may have a duration of about 10 seconds.

In some non-limiting examples, a frequency domain pulse strength metric may be determined by choosing 455 a data window to delimit a portion of the biological signal, determining 460 a spectrum analysis of the portion of the biological signal delimited by the data window, filtering 465 one or more spectral peaks calculated from the spectrum analysis, identifying 465 a spectral peak having a central frequency of about a pulse rate from the spectrum analysis, identifying a spectral peak having a central frequency of about a respiration rate from the spectrum analysis, and identifying, 475 a spectral power of the spectral peak having a central frequency of about a pulse rate of the human body.

In some non-limiting examples, the data window may have a fixed value of time or number of digitized samples of the biological signal. In one non-limiting example, the data window may have a duration of about 5 seconds to about 30 seconds. Non-limiting examples of such a window durations may include about 5 seconds, about 10 seconds, about 15 seconds, about 20 seconds, about 25 seconds, about 30 seconds, and ranges between any two of these values including endpoints. In one non-limiting example, the data window may have a duration of about 10 seconds. In other non-limiting examples, the data window may be calculated by the computing device. In one non-limiting example, the data window may be calculated from a respiratory period. It may be understood, that the respiratory period may be calculated from the inverse of the frequency of the respiration rate. The respiratory period may be determined from a respirometer or from the peak at about the respiratory frequency determined by the power spectrum.

In some non-limiting examples, a time domain pulse rate metric may be determined by identifying 415 a plurality of signal peaks within the biological signal, identifying 435 a time occurrence for each of the plurality of signal peaks, and determining 440 a plurality of time differences, wherein each time difference is determined from a first time occurrence of the first peak and a second time occurrence of a second peak. In some embodiments, the method may additionally include determining, an average time difference of a portion of the plurality of time differences, and determining 445 an inverse (or reciprocal) of the average time difference. In an alternative embodiment, the computing device may determine an inverse (or reciprocal) of each time difference of the plurality of time difference and calculate an average of the inverse time differences.

In one example, the computing device may calculate an average time difference of a plurality of time differences around each of the signal peaks within a data window. In another example, the computing device may calculate an average inverse time difference of a plurality of inverse time differences around each of the signal peaks within a data window. In one non-limiting example, the data window may comprise a time duration equal to at least one respiratory cycle of a patient being monitored. In one non-limiting example, the data window may have a duration of about 5 seconds to about 30 seconds. Non-limiting examples of such a window durations may include about 5 seconds, about 10 seconds, about 15 seconds, about 20 seconds, about 25 seconds, about 30 seconds, and ranges between any two of these values including endpoints. In one non-limiting example, the data window may have a duration of about 10 seconds.

In some non-limiting examples, a frequency domain pulse rate metric may be determined by choosing 455 a data window to delimit a portion of the biological signal, determining 460 a spectrum analysis of the portion of the biological signal delimited by the data window, filtering 465 one or more spectral peaks calculated from the spectrum analysis, and identifying 465 a spectral peak having a central frequency of about a pulse rate from the spectrum analysis.

In some non-limiting examples, the data window may have a fixed value of time or number of digitized samples of the biological signal. In one non-limiting example, the data window may have a duration of about 5 seconds to about 30 seconds. Non-limiting examples of such a window durations may include about 5 seconds, about 10 seconds, about 15 seconds, about 20 seconds, about 25 seconds, about 30 seconds, and ranges between any two of these values including endpoints. In one non-limiting example, the data window may have a duration of about 10 seconds. In other non-limiting examples, the data window may be calculated by the computing device. In one non-limiting example, the data window may be calculated from a respiratory period. It may be understood, that the respiratory period may be calculated from the inverse of the frequency of the respiration rate. The respiratory period may be determined from a respirometer or from the peak at about the respiratory frequency determined by the power spectrum.

Figure 5:
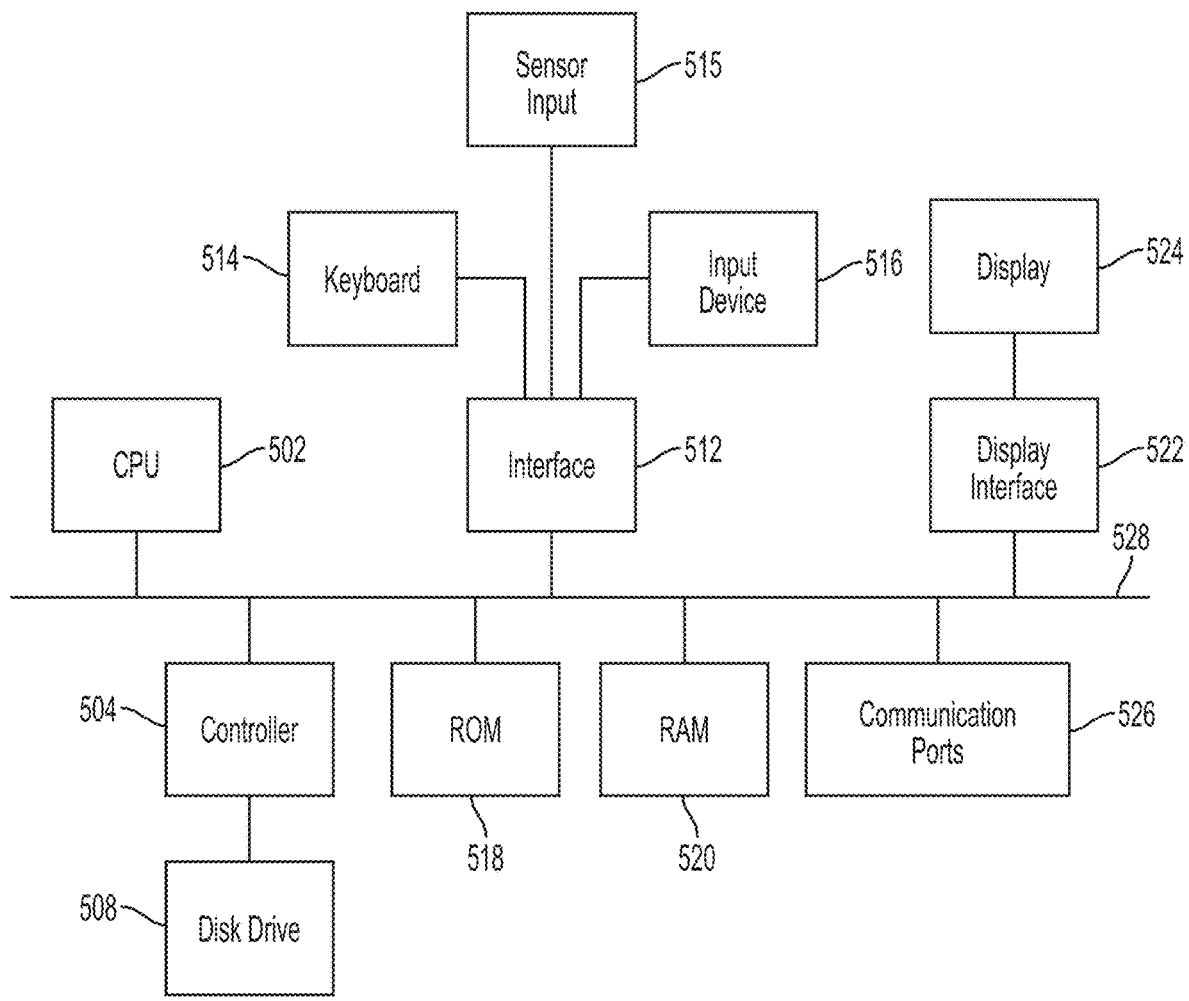
FIG. 5 depicts a schematic of a computing device in accordance with some embodiments.

FIG. 5 is a block diagram of an embodiment of at least some components that may compose the computing device. Referring to FIG. 5, a bus 528 may serve as the main information highway interconnecting the other illustrated components of the hardware. CPU 502 is the central processing unit of the system, performing calculations and logic operations required to execute at least some calculations for the method. Read only memory (ROM) 518 is one non-limiting example of a static or non-transitory memory device, and random access memory (RAM) 520 is one non-limiting example of a transitory or dynamic memory device.

A controller 504 may interface the system bus 528 with one or more optional disk drives 508. These disk drives may include, for example, external or internal DVD drives, CD ROM drives, or hard drives.

Program instructions for calculations or other computing device functions may be stored in the ROM 518 and/or the RAM 520. Optionally, program instructions may be stored on one or more computer readable media such as a compact disk, a digital disk, and other recordable media. Alternatively, program instructions may be provided to the computing device via a communications signal or a carrier wave. Additionally, pulse volume waveform data or other data used by the computing device may be stored on one or more removable memory devices that may include, as non-limiting examples, a removable disc, a removable card, a removable memory stick, a flash drive, a removable SIM chip, a writable CD-ROM or DVD disk, and/or a miniature data tape. Such devices may be used to transfer data from the computing device to another data receiving device such as a home computer.

An optional display interface 522 may permit information from the bus 528 to be displayed on a display device 524 in audio, graphic, or alphanumeric format. Additional output interface devices may include a printer, a barcode printer, an LCD panel device, a touch screen device, an audio device, an LED panel, an OLED panel device, one or more individual LEDs, either as separate displays or grouped together, and a haptic device. Communication with external devices may occur using various communication ports 526.

In addition to the components disclosed above, the computing device may also include an interface 512 which may allow for receipt of data from input devices such as a keyboard 514 or other input devices 516 such as a touch screen, a mouse, a remote control, a pointing device, a pushbutton, a haptic device, a voice recognition device, a proximity sensor, a motion detection sensor, a directional pad, and/or a joystick.

In addition, biological signals acquired by a pulse volume sensor or other sensors of biological signals may be communicated to the computing device via a sensor input 515 through the interface 512 to the bus 528. Such biological signals may be presented to the computing device as either analog signals or digital signals. If the pulse volume sensor provides analog biological signals, the computing device may also include hardware components configured to convert the analog signals into digital signals. Non-limiting examples of such hardware components may include one or more of a sample and hold device, an analog-to-digital converter, and a voltage reference. Such hardware components may be present as independent devices, one or more combination devices, or one or more detachable modules that may be placed in data communication with the sensor input 515, the interface 512, or the bus 528. If the pulse volume sensor provides digital biological signals, the computing device may include one or more separate digital interfaces to receive the digital biological signals. Such digital interfaces may include, without limitation, one or more of a parallel interface, a serial interface, an IR interface, a radio frequency interface, and a personal area network interface.

It may be appreciated that such a computing device may receive sensor data from additional biological signal detectors including, without limitation, an ECG device, a patient temperature measurement device, a patient respiratory measurement device, a patient blood pressure measurement device, a patient pulse rate measurement device, and a patient heart rate measurement device. In some embodiments, biological signal data from these or other biological signal detecting devices may be used as part of the method for identifying or characterizing cardiac bradycardia behavior.

It may be recognized that a computing device such as one depicted in FIG. 5 may be used as a basis for system for predicting a hypovolemic hypotensive condition resulting for cardiac bradycardia behavior. Such a system may include, without limitation at least one sensor in data communication with a human body, the at least one sensor configured to receive a biological signal emulating an arterial pulse wave from the human body, a computing device in operable communication with the at least one sensor, a non-transitory, computer-readable storage medium in operable communication with the computing device, an input device in operable communication with the computing device, and an output device in operable communication with the computing device. The computer-readable storage medium may also contain one or more programming instructions that, when executed, cause the computing device to receive a biological signal emulating an arterial pulse wave from the sensor, determine a plurality of pulse rate metrics from the biological signal, determine a plurality of pulse strength metrics from the biological signal, determine a plurality of pulse rate differences, wherein each pulse rate difference is determined from a first pulse rate metric and a pulse rate baseline, determine a plurality of pulse strength differences, wherein each pulse strength difference is determined from a first pulse strength metric and a pulse strength baseline, and predict a hypovolemic hypotensive condition resulting from cardiac bradycardia behavior in the human body in response to at least one anomalous pulse rate difference and at least one anomalous pulse strength difference. Additionally, the one or more programming instructions may include programming instructions that, when executed, cause the computing device to determine one or more of the pulse strength baseline, the pulse strength threshold, the pulse rate baseline, and the pulse rate threshold.

The computing device may also be configured to receive data from additional devices such as from one or more therapeutic devices including, for example, a dialysis device or a ventilator. Data from such therapeutic devices may be included in one or more output displays by the computing device to assist a health care professional in correlating a cardiac dysrhythmia behavior with the operation of the one or more therapeutic devices. In some non-limiting examples, the computing device may include instructions to predict possible cardiac dysrhythmia behavior based on data from the one or more therapeutic devices along with biological signal data from the one or more biological signal detecting devices.

It may be further understood that biological signal data and parameters derived therefrom, including pulse rate metrics, pulse strength metrics, baseline values, threshold values, event warning annotations associated with patient data, and other calculated, determined, or derived values, may all be stored in one or more memory devices, removable memory devices, or disk drives included in the computing device. Alternatively, all such data may be stored in one or more server devices accessible by the computing device over one or more of internet, intranet, and personal network interfaces.

EXAMPLES

Example 1: An Output Display of Patient Data for a Patient Undergoing Dialysis Therapy It may be understood that an output display of patient data by a computing device may include data related to patient physiological status in addition to annotations related to, but not limited to, date and time, patient identification information, patient diagnosis information, warning indicators, arrhythmia event indicators, and data associated with a therapeutic device if the patient is undergoing a therapeutic procedure during pulse wave monitoring. In some embodiments, the computing device may display on an output device a representation of a portion of the biological signal along with at least one annotation identifying the cardiac bradycardia behavior. In some embodiments the biological signal displayed on the output device may be updated over time. In some embodiments, the computing device may display on the output device one or more annotations including a hypovolemia indicator and a hypotensive indicator. In still other embodiments, the computing device may provide one or more warnings to a user if the cardiac bradycardia behavior indicates an emergent condition associated with the human body.

Figure 6:
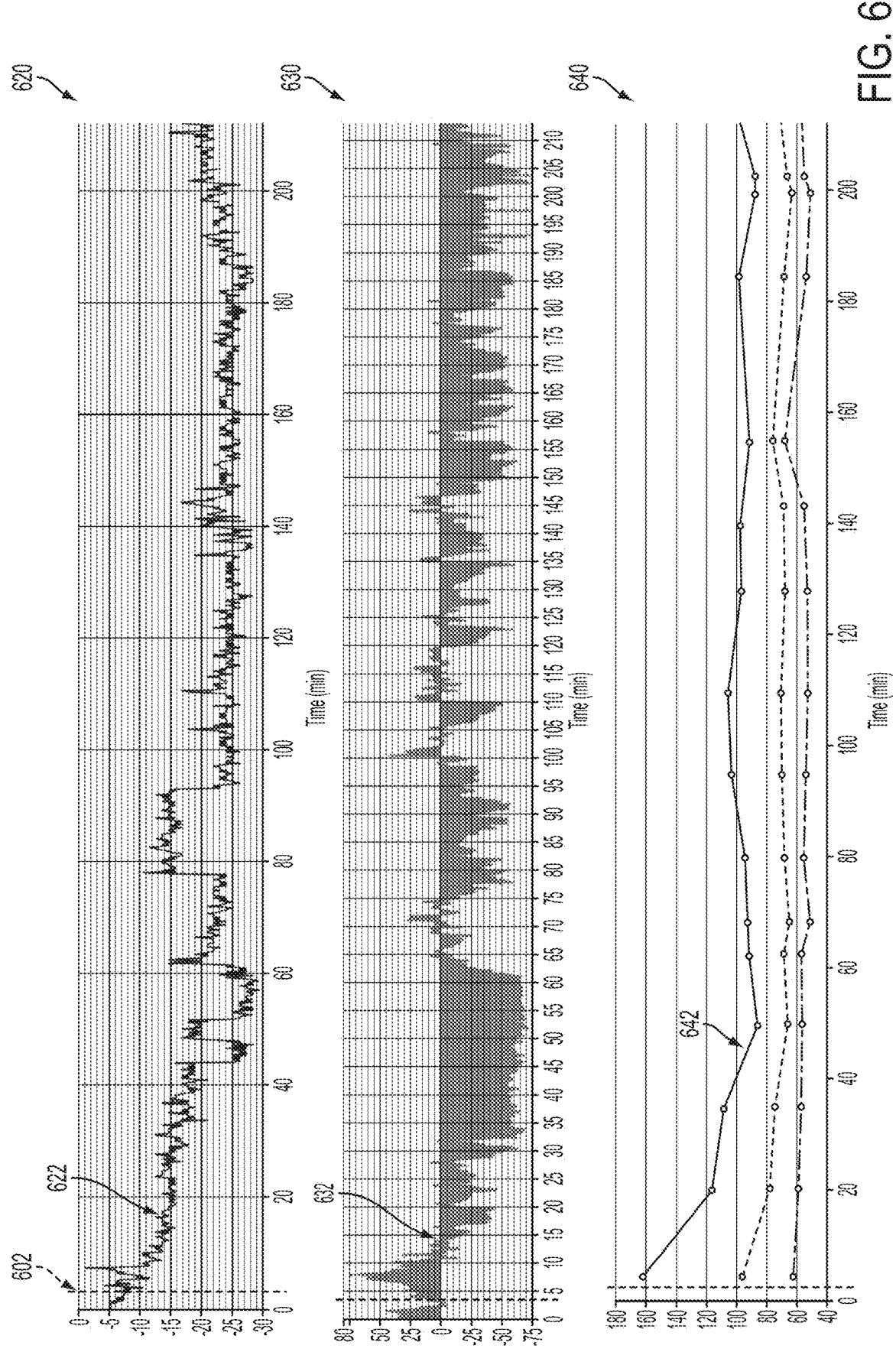
FIG. 6 depicts an output display of patient data for a patient undergoing dialysis therapy in accordance with some embodiments.

FIG. 6 illustrates a non-limiting example of a computing device real-time output display to indicate the status of an end-stage renal disease patient undergoing dialysis. Exemplary data presented on such a display may include a trace of the percent change in a patient pulse rate 620, a trace of the percent changes in a patient pulse strength 630, and a trace of the patient blood pressure 640. The time axis of each display is indicated as time, in minutes, after the start of the dialysis treatment 602.

An indicator regarding patient status, such as a warning indicator, may also be provided to a user of the computing device. The warning indicator may be triggered if any data associated with patient status, including data associated with pulse waveform peak amplitude differences, pulse waveform peak time differences, and one or more time difference dispersion metrics meet one or more warning criteria. The warning criteria may be used by the health care provider as an indicator of a potential hypovolemic hypotensive condition resulting from cardiac bradycardia behavior. The health care provider may then assess the usefulness of continuing the therapeutic procedure or stop the procedure depending on the hemodynamic instability risk of the procedure to the patient.

Additional metrics associated with patient status, such as metrics associated with patient ventilation and patient blood chemistry (for example, additional blood gas metrics), may also be displayed. In one non-limiting example, such displays may be presented in real time by scrolling the data presented on the display.

Such a patient status display may also permit a health care provider and system user to display selected data presented during defined time windows. Such time windows may include an entire therapeutic session, a portion of a therapeutic session, or a time window including pre-therapy time, therapy time, and post-therapy time. Thus, such a display window may display data generally over any time interval, including, without limitation, a time window for intervals of about 1 minute to about 24 hours. Non-limiting examples of such time window intervals may include time intervals of about 1 minute, about 2 minutes, about 5 minutes, about 10 minutes, about 20 minutes, about 30 minutes, about 1 hour, about 2 hours, about 5 hours, about 10 hours, about 20 hours, about 24 hours, and ranges between any two of these values including endpoints.

For example, in FIG. 6, an anomalous decrease in the percent change in the pulse rate 620 may be observed at an early time in the dialysis procedure. In some embodiments, the pulse rate metric may be calculated as a difference between the pulse rate and the pulse rate baseline. In alternative embodiments, the pulse rate metric may be calculated as a percent change in pulse rate defined as a difference between the pulse rate and the pulse rate baseline, the difference being normalized to (divided by) the pulse rate baseline value. In one non-limiting example, a percent change in pulse rate threshold may be set as a fraction of the value of the pulse rate baseline. In the trace of the percent change in a patient pulse rate 620, the pulse rate threshold is set to −15%. It may be observed that the percent change in pulse rate decreases to the threshold 622 at around minute 15 of the procedure.

Similarly, an anomalous decrease in the percent change in the pulse strength 630 may be observed at an early time in the dialysis procedure. In some embodiments, the pulse strength metric may be calculated as a difference between the pulse strength and the pulse strength baseline. In alternative embodiments, the pulse strength metric may be calculated as a percent change in pulse strength defined as a difference between the pulse strength and the pulse strength baseline, the difference being normalized to (divided by) the pulse strength baseline value. In one non-limiting example, a percent change in pulse strength threshold may be set as a fraction of the value of the pulse strength baseline. In the trace of the percent change in a patient pulse strength 630, the pulse strength threshold is also set to −15%. It may be observed that the percent change in pulse strength decreases to the threshold 632 at around minute 15 of the procedure.

It may be observed that the trace of the patient blood pressure 640 depicts a drop in systolic blood pressure (top line in the trace 640) to less than 100 mm Hg (about 13 kPa) 642 at about minute 50 of the procedure. Such a low systolic blood pressure, indicative of a hypotensive state in the patient, may result from a therapeutic procedure, such as induced hypovolemia during dialysis. The percent change in pulse rate and the percent change in pulse strength reach their threshold values (622 and 632, respectively) about 30 minutes before the blood pressure measurement indicates a potential hypotensive condition 642. A health care provider, thereby forewarned of possible hypotensive events, may adjust or even terminate the therapy to prevent additional trauma to the patient.

It may be understood that a user may control the display of patient status information provided by the computing device, such as a display of status data, types of data analysis results, and annotations of data analysis results. In one non-limiting example, a drop-down menu may be used by a user to indicate which types of information, analyses, and annotations may be displayed.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated in this disclosure, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can, of course, vary. It is also to be understood that the terminology used in this disclosure is for the purpose of describing particular embodiments only, and is not intended to be limiting.

With respect to the use of substantially any plural and/or singular terms in this disclosure, those having skill in the art can translate from the plural to the singular and/or from the singular to the plural as is appropriate to the context and/or application. The various singular/plural permutations may be expressly set forth in this disclosure for sake of clarity.

It will be understood by those within the art that, in general, terms used in this disclosure, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or an (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed in this disclosure also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed in this disclosure can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

From the foregoing, it will be appreciated that various embodiments of the present disclosure have been described for purposes of illustration, and that various modifications may be made without departing from the scope and spirit of the present disclosure. Accordingly, the various embodiments disclosed are not intended to be limiting, with the true scope and spirit being indicated by the following claims.

What is claimed is:

1. A method for predicting a hemodynamic instability condition for a patient resulting from cardiac behavior, the method comprising:

receiving, by a computing device, a biological signal emulating an arterial pulse wave from a sensor in data communication with a human body;

performing a frequency spectrum analysis on the biological signal in a plurality of data windows over time and generating a frequency spectrum having a plurality of spectral peaks at frequencies in the frequency spectrum, each with a spectral power;

evaluating the frequency spectrum and determining, by the computing device, a plurality of pulse rate metrics from the biological signal based on the spectral peaks in the spectrum analysis over the plurality of data windows;

determining, by the computing device, a plurality of pulse strength metrics from the biological signal based on a spectral power of the spectral peaks in the spectrum analysis over the plurality of data windows;

determining a pulse rate baseline and a pulse strength baseline based on the pulse rate metrics and on the pulse strength metrics, respectively, for early data windows;

determining, by the computing device, a plurality of pulse rate differences, wherein each pulse rate difference is determined from pulse rate metrics of data windows subsequent to the early data windows and the pulse rate baseline;

determining, by the computing device, a plurality of pulse strength differences, wherein each pulse strength difference is determined from pulse strength metrics of data windows subsequent to the early data windows and the pulse strength baseline;

determining a threshold associated with the pulse strength differences;

determining a threshold associated with the pulse rate differences;

comparing at least one anomalous pulse rate difference with the pulse rate difference threshold to determine when the pulse rate difference decreases below the pulse rate threshold;

comparing at least one anomalous pulse strength difference with the pulse strength difference threshold to determine when the pulse strength difference decreases below the pulse strength threshold; and identifying, by the computing device, the hemodynamic instability condition resulting from cardiac behavior in the human body based upon the simultaneous decrease of the at least one anomalous pulse rate difference and the at least one anomalous pulse strength difference below the respective thresholds; and upon the identification of the hemodynamic instability condition alerting a caregiver with an output device coupled with the computing device to take action to prevent trauma to the patient.

2. The method of claim 1, wherein receiving a biological signal emulating an arterial pulse wave from a sensor comprises receiving a biological signal emulating an arterial pulse wave from one or more of a plethysmograph, a photoplethysmograph, a transmittance photo-optic sensor, a reflective photo-optic sensor, a pressure transducer, a strain gauge, an ultrasound device, a radar device, a sphygmomanometer, and an ECG device.

3. The method of claim 1, wherein determining a pulse rate metric from the biological signal comprises:
    filtering, by the computing device, one or more spectral peaks from the spectrum analysis;
    identifying, by the computing device, a spectral peak having a central frequency of about a pulse rate of the human body from the spectrum analysis; and
    identifying, by the computing device, a spectral peak having a central frequency of about a respiration rate of the human body from the spectrum analysis.

4. The method of claim 1, further comprising determining, by the computing device, the data window from the respiration rate.

5. The method of claim 1, wherein determining a pulse strength metric from the biological signal comprises:
    filtering, by the computing device, one or more spectral peaks from the spectrum analysis;
    identifying, by the computing device, a spectral peak having a central frequency of about a pulse rate from the spectrum analysis;
    identifying, by the computing device, a spectral peak having a central frequency of about a respiration rate from the spectrum analysis; and
    identifying, by the computing device, a spectral power of the spectral peak having a central frequency of about a pulse rate of the human body.

6. The method of claim 5, further comprising determining, by the computing device, the data window from the respiration rate.

7. The method of claim 1, wherein determining the pulse rate baseline comprises:
    identifying a plurality of signal peaks within a data window of the biological signal, wherein the data window includes a period of a normative cardiac rhythm;
    identifying a time occurrence for each of the plurality of signal peaks;
    determining a plurality of time differences, wherein each time difference is determined from a first time occurrence of the first peak and a second time occurrence of a second peak;
    determining an average time difference from the plurality of time differences;
    and determining an inverse of the average time difference.

8. The method of claim 1, wherein determining the pulse strength baseline comprises:
    performing the frequency spectrum analysis of a portion of the biological signal within an initial plurality of windows that include a period of a normative cardiac rhythm of the human body;
    filtering one or more spectral peaks from the spectrum analysis;
    identifying a spectral peak having a central frequency of about a pulse rate of the human body from the frequency spectrum analysis; and
    determining the pulse strength baseline from a spectral power of the identified spectral peak.

9. The method of claim 1, wherein determining the pulse strength baseline comprises:
    performing the frequency spectrum analysis within an initial plurality of data windows, wherein each of the initial plurality of data windows includes a period of a normative cardiac rhythm of the human body;
    filtering one or more of the plurality of spectral peaks, each of the plurality of spectral peaks being obtained from one of the frequency spectrum analyses over the initial plurality of data windows;
    identifying another plurality of spectral peaks, each spectral peak having a central frequency of about a pulse rate of the human body from one of the spectrum analyses over the initial plurality of data windows; and
    determining the pulse strength baseline from an average of a spectral powers, each spectral power being determined from one of the plurality of identified spectral peaks.

10. The method of claim 1, wherein determining the pulse rate threshold comprises subtracting a pulse rate factor times the pulse rate baseline from the pulse rate baseline.

11. The method of claim 10, wherein subtracting a pulse rate factor from the pulse rate baseline comprises subtracting a pulse rate factor greater than zero and less than or equal to 1 times the pulse rate baseline from the pulse rate baseline.

12. The method of claim 10, wherein subtracting a pulse rate factor from the pulse rate baseline comprises subtracting a value of about 0.15 times the pulse rate baseline from the pulse rate baseline.

13. The method of claim 10, wherein subtracting a pulse rate factor from the pulse rate baseline comprises subtracting a pulse rate factor times the pulse rate baseline from the pulse rate baseline, wherein the pulse rate factor is stored in a library of pulse rate baseline factors.

14. The method of claim 1, wherein determining the pulse strength threshold comprises subtracting a pulse strength factor times the pulse strength baseline from the pulse strength baseline.

15. The method of claim 14, wherein determining the pulse strength threshold comprises subtracting a pulse strength factor greater than zero and less than or equal to 1 times the pulse strength baseline from the pulse strength baseline.

16. The method of claim 14, wherein determining the pulse strength threshold comprises subtracting a pulse strength factor of about 0.15 times the pulse strength baseline from the pulse strength baseline.

17. The method of claim 14, wherein subtracting a pulse strength factor from the pulse strength baseline comprises subtracting a pulse strength factor times the pulse strength baseline from the pulse strength baseline, wherein the pulse strength factor is stored in a library of pulse strength baseline factors.

18. The method of claim 1, further comprising displaying, by the computing device on an output device, a representation of a portion of the biological signal along with at least one annotation identifying the hemodynamic instability condition.

19. The method of claim 18, wherein displaying the representation of the portion of the biological signal comprises updating the representation of the portion of the biological signal over time.

20. The method of claim 18, wherein the annotation identifying the hemodynamic instability condition is one or more of a hypovolemia indicator and a hypotensive indicator.

21. The method of claim 1, further comprising issuing, by the computing device, a warning that a hemodynamic instability condition indicates an emergent condition associated with the human body.

22. A system for predicting a hemodynamic instability condition for a patient resulting from cardiac behavior, the system comprising:
- at least one sensor configured for data communication with a human body, the at least one sensor configured to receive a biological signal emulating an arterial pulse wave from a human body;
- a computing device in operable communication with the at least one sensor;
- a non-transitory, computer-readable storage medium in operable communication with the computing device;
- an input device in operable communication with the computing device;
- an output device in operable communication with the computing device;

wherein the computer-readable storage medium contains one or more programming instructions that, when executed, cause the computing device to:
- receive a biological signal emulating an arterial pulse wave from the sensor;
- perform a frequency spectrum analysis on the biological signal in a plurality of data windows over time and generating a frequency spectrum having a plurality of spectral peaks at frequencies in the frequency spectrum, each with a spectral power;
- evaluate the frequency spectrum and determine a plurality of pulse rate metrics from the biological signal based on the spectral peaks in the spectrum analysis over the plurality of data windows;
- determine a plurality of pulse strength metrics from the biological signal based on a spectral power of the spectral peaks in the spectrum analysis over the plurality of data windows;
- determine a pulse rate baseline and a pulse strength baseline based on the pulse rate metrics and on the pulse strength metrics, respectively, for early data windows;
- determine a plurality of pulse rate differences, wherein each pulse rate difference is determined from pulse rate metrics of data windows subsequent to the early data windows and the pulse rate baseline;
- determine a plurality of pulse strength differences, wherein each pulse strength difference is determined from pulse strength metrics of data windows subsequent to the early data windows and the pulse strength baseline;
- determine a threshold associated with the pulse strength differences;
- determine a threshold associated with the pulse rate differences;
- compare at least one anomalous pulse rate difference with the pulse rate difference threshold to determine when the pulse rate difference decreases below the pulse rate threshold;
- compare at least one anomalous pulse strength difference with the pulse strength difference threshold to determine when the pulse strength difference decreases below the pulse rate threshold;
- identify a hemodynamic instability condition resulting from cardiac behavior in the human body based upon the simultaneous decrease of the at least one anomalous pulse rate difference and the at least one anomalous pulse strength difference below the respective thresholds; and
- upon the identification of the hemodynamic instability condition alerting a caregiver with the output device coupled with the computing device to take action to prevent trauma to the patient.

* * * * *